US008943837B2

(12) United States Patent
Care et al.

(10) Patent No.: US 8,943,837 B2
(45) Date of Patent: Feb. 3, 2015

(54) FLUID MANAGEMENT APPARATUS AND METHOD

(75) Inventors: Ian C. D. Care, Derby (GB); John D. Black, Ashbourne (GB)

(73) Assignee: Rolls-Royce PLC, London (GB)

( * ) Notice: Subject to any disclaimer, the term of this patent is extended or adjusted under 35 U.S.C. 154(b) by 473 days.

(21) Appl. No.: 13/604,086

(22) Filed: Sep. 5, 2012

(65) Prior Publication Data

US 2014/0026583 A1 Jan. 30, 2014

(30) Foreign Application Priority Data

Sep. 22, 2011 (GB) .................................. 1116351.6

(51) Int. Cl.

*F01D 25/18* (2006.01)
*B64C 1/14* (2006.01)
*H05B 6/80* (2006.01)
*G01N 21/84* (2006.01)
*B64D 33/04* (2006.01)

(52) U.S. Cl.

CPC .............. *F01D 25/18* (2013.01); *B64C 1/1453* (2013.01); *H05B 6/80* (2013.01); *G01N 21/84* (2013.01); *B64D 33/04* (2013.01)
USPC ........................................... 60/772; 60/39.08

(58) Field of Classification Search

CPC ...... B64C 1/1453; B64D 33/04; F01D 25/18; G01N 21/84; H05B 6/80
USPC ........... 60/39.08, 772, 801; 244/53 R; 702/40
See application file for complete search history.

(56) References Cited

U.S. PATENT DOCUMENTS

| | | | | |
|---|---|---|---|---|
| 5,080,303 | A * | 1/1992 | Hutton | 244/53 R |
| 5,974,860 | A * | 11/1999 | Kuroda et al. | 73/40 |
| 6,116,015 | A * | 9/2000 | Taylor et al. | 60/39.08 |
| 6,513,332 | B2 | 2/2003 | Care et al. | |
| 2002/0178729 | A1 * | 12/2002 | Care et al. | 60/772 |
| 2004/0200265 | A1 | 10/2004 | Eden et al. | |
| 2009/0133376 | A1 * | 5/2009 | Zysman | 60/39.08 |

OTHER PUBLICATIONS

British Search Report issued in British Patent Application No. 1116351.6 dated Dec. 20, 2011.

* cited by examiner

*Primary Examiner* — Phutthiwat Wongwian
*Assistant Examiner* — Marc J Amar
(74) *Attorney, Agent, or Firm* — Oliff PLC

(57) ABSTRACT

A fluid management apparatus and method, the apparatus including: a fluid conduit for the passage of a dispersion containing particulate matter; a laser arranged to provide laser light inside the fluid conduit; wherein, in use, the laser light heats the particulate matter sufficiently to generate incandescence; one or more sensors for detecting the incandescence of the particulate matter so as to determine a characteristic of the dispersion; and an electromagnetic wave generator operable to provide electromagnetic waves inside the fluid conduit at a position downstream of the laser light so as to vaporize at least a portion of the dispersion.

14 Claims, 1 Drawing Sheet

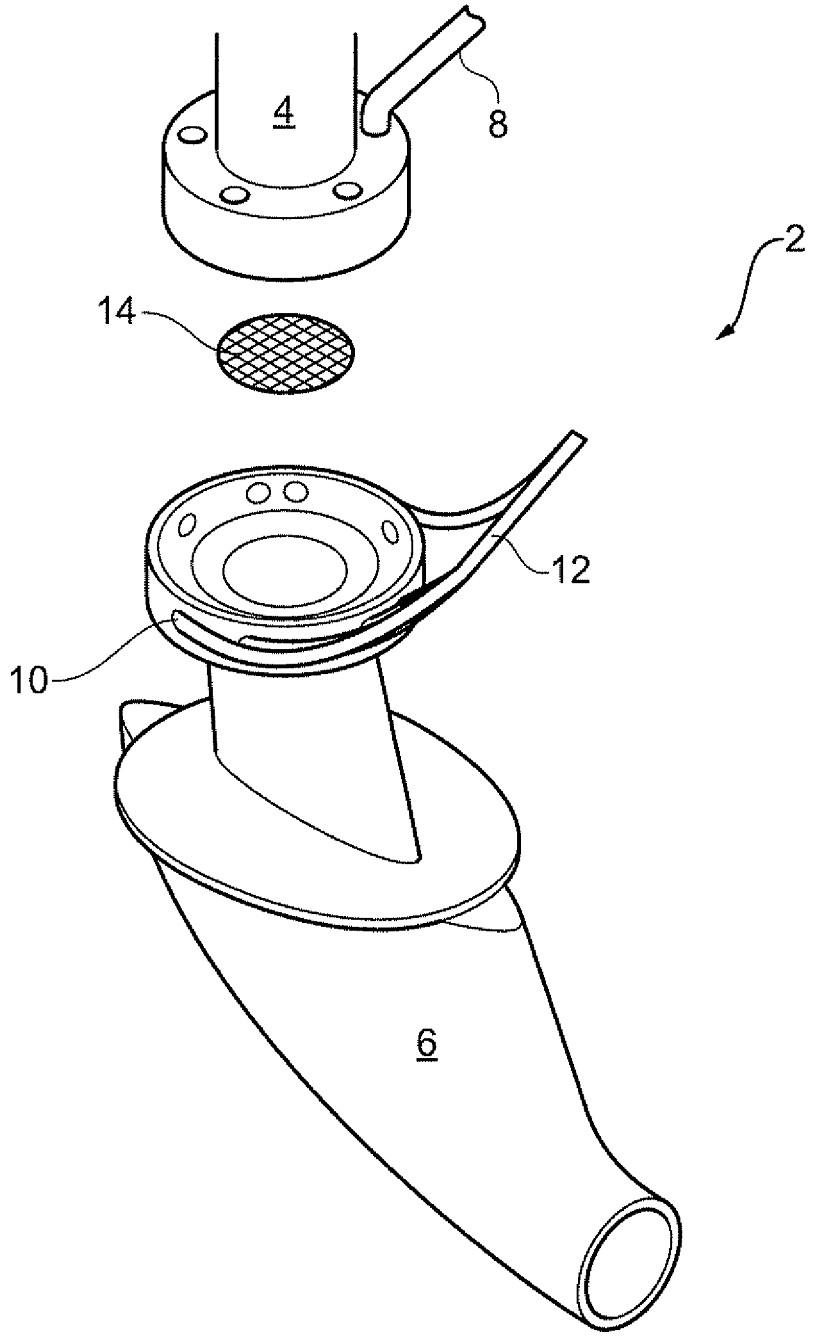
4
8
2
14
12
10
6

FLUID MANAGEMENT APPARATUS AND METHOD

The present invention relates to a fluid management apparatus and method, and particularly, but not exclusively, to a fluid management apparatus and method for use with a gas turbine engine.

BACKGROUND

Under normal operating conditions, a bearing chamber of a gas turbine engine typically contains a lubricating oil. Pressurised seals are used to prevent oil leakage from the bearing chambers into the rest of the engine. With such a seal, the bearing chamber is held under a negative pressure. To maintain the negative pressure, air is bled out of the bearing chamber. The air bled from the bearing chamber typically contains an amount of oil in the form of droplets or particles. This mixture of air and oil droplets is then passed to an oil/air separator, such as a centrifuge which rotates at high speed. The separated oil is returned to the lubrication system while the air is discharged overboard through a breather outlet.

Although, in general, oil/air separators are unable to remove absolutely all of the oil from the air which is discharged overboard, it is desirable to improve the efficiency of the separator in order to reduce the environmental impact of the engine. However, high efficiency separators effectively eliminate oil consumption, which over time can cause the oil to thermally degrade, becoming acidic and leaving deposits around the oil system. Furthermore, the oil can become less effective at performing its function of heat and debris transference. To overcome this problem, it is necessary to monitor the oil to identify when partial or full oil change is required.

Moreover, the oil/air mixture discharged overboard may have the appearance of smoke, particularly when the aircraft is stationary or moving relatively slowly. This may cause distress to passengers as the smoke may be mistakenly assumed to be a problem with the engine. Furthermore, the oil/air mixture may cause unsightly staining of the engine nacelle as it is discharged overboard and may also stain the runway surface.

U.S. Pat. No. 6,513,332 discloses a breather outlet comprising an electromagnetic wave (e.g. microwave) generator which is used to evaporate at least a portion of the liquid dispersion. However, whilst the breather outlet is able to reduce the appearance of smoke, it does not provide any quantitative information regarding the egress of oil from the engine.

It is therefore desirable to provide a fluid management apparatus and method which is able to analyse the oil flow out of the engine and to prevent smoke from forming.

STATEMENTS OF INVENTION

In accordance with an aspect of the invention there is provided a fluid management apparatus comprising: a fluid conduit for the passage of a dispersion containing particulate matter; a laser arranged to provide laser light inside the fluid conduit; wherein, in use, the laser light heats the particulate matter sufficiently to generate incandescence; one or more sensors for detecting the incandescence of the particulate matter so as to determine a characteristic of the dispersion; and an electromagnetic wave generator operable to provide electromagnetic waves inside the fluid conduit at a position downstream of the laser light so as to vaporise at least a portion of the dispersion.

The electromagnetic wave generator may also be operable to provide electromagnetic waves inside the fluid conduit at a position upstream of the laser light so as to perform a scattering measurement.

A single electromagnetic generator may provide the electromagnetic waves both upstream and downstream of the laser light (i.e. where the laser light impinges on the particulate matter).

The output of the electromagnetic wave generator may be split and directed upstream and downstream of the laser light. The dual use of the electromagnetic wave generator may reduce the size, weight and cost of the apparatus.

The output may be split by a waveguide splitter.

The intensity of the electromagnetic waves may be lower at the upstream position than at the downstream position. By using a lower intensity at the upstream position, the electromagnetic waves may be scattered by the particulate matter rather than vaporising the particulate matter.

The fluid management apparatus may further comprise an attenuator for attenuating the electromagnetic waves directed towards the upstream position.

The electromagnetic wave generator may be a microwave generator.

The one or more sensors may be coupled to the fluid conduit by optical fibres. This may allow the sensors to be located remotely, thus improving the robustness of the apparatus.

The sensors may be electronically or optically multiplexed. This may reduce the weight of the apparatus. Each sensor may be configured to detect only a certain frequency or frequencies of light and thus be configured to detect different types of particulate matter.

The laser may be configured to provide a first relatively low power pulse and a second relatively high power pulse to the particulate matter.

The first pulse may be a preheat pulse and the second pulse may induce incandescence in the particulate matter.

The same laser or lasers may provide both the first and second pulses. The dual use of the laser may reduce the size, weight and cost of the apparatus.

The laser may be a continuous wave laser. The continuous wave laser may have a higher fluence than a pulsed laser. The high fluence of a continuous wave laser may allow heat to be supplied to the particulate matter at the same time as it is being lost to the surrounding gas. This may allow single particles to be detected as they pass through the continuous wave laser beam.

The fluid management apparatus may further comprise a second laser, and the lasers may intersect one another inside the fluid conduit.

The lasers may be diametrically opposed.

The characteristic of the dispersion may include one or more of (i) composition; (ii) size of the particulate matter; (iii) volume fraction of particulate matter; (iv) flow rate of the dispersion; (v) flight time of the particulate matter; (vi) increase in temperature of the particulate matter; and (vii) fluid conduit discharge pressure.

The fluid management apparatus may further comprise a safety interlock which may prevent the laser and/or electromagnetic wave generator from operating if the apparatus is not assembled or is misassembled. Furthermore, electromagnetic wave containment means, such as a wire mesh (faraday cage), may be provided to prevent the electromagnetic waves from exiting the fluid conduit. A second mesh may be provided to prevent electromagnetic waves travelling outside the measurement and vaporisation zone.

The fluid conduit may form part of a breather outlet of a gas turbine engine, for example.

In accordance with another aspect of the invention there is provided a fluid management method comprising: passing a dispersion containing particulate matter through a fluid conduit; heating the particulate matter with laser light to generate incandescence; detecting the incandescence of the particulate matter to determine a characteristic of the dispersion; and vaporising at least a portion of the dispersion using electromagnetic waves.

The fluid management method may further comprise passing electromagnetic waves through the dispersion to perform a scattering measurement prior to heating the particulate matter with laser light.

A single electromagnetic wave generator may provide the electromagnetic waves both upstream and downstream of the laser light.

The particulate matter may be heated with a first relatively low power pulse of laser light and a second relatively high power pulse of laser light.

The first pulse may be a preheat pulse and the second pulse may induce incandescence in the particulate matter. For example, the second pulse may induce incandescence in at least one droplet of the particulate matter.

BRIEF DESCRIPTION OF THE DRAWINGS

For a better understanding of the present disclosure, and to show more clearly how it may be carried into effect, reference will now be made, by way of example, to the accompanying drawing, in which:

FIG. 1 is an exploded perspective view of a breather outlet according to an embodiment of the invention.

DETAILED DESCRIPTION

With reference to FIG. 1, a fluid management apparatus according to an embodiment of the invention comprises a breather outlet 2 for a gas turbine engine.

The gas turbine engine comprises an oil or lubrication system, as known in the art, which maintains a supply of oil to engine components, such as a bearing chamber (not shown). As discussed previously, the bearing chamber is held under a negative pressure to ensure oil does not undesirably escape from the chamber into the rest of the engine. To maintain the negative pressure, air is bled out of the bearing chamber. The air bled from the bearing chamber contains droplets of oil. This mixture of air and oil is passed to an oil/air separator, such as a centrifugal vane separator which rotates at high speed to separate the oil from the air. The separated oil is returned to the lubrication system while the air is discharged overboard via the breather outlet 2. The breather outlet 2 therefore provides fluid communication between the interior and exterior of the engine across the engine nacelle.

The breather outlet 2 comprises an upper generally cylindrical portion 4 and a lower generally cylindrical portion 6 which, in use, are connected to form a fluid conduit.

The breather outlet 2 is positioned downstream of the oil/air separator. Whilst the majority of the oil is separated from the air, a small amount of oil remains forming a dispersion of air and oil. In general this is in the form of droplets of less than 12 microns in diameter. The dispersion flows into the fluid conduit via the upper portion 4 and is discharged overboard via the lower portion 6.

The dispersion may also contain other particulate matter such as airborne contaminants that have been ingested into the engine. Furthermore, the presence of other contaminants may be indicative of problems elsewhere in the engine, such as fuel (heat exchanger damage), water, silica (seal wear), hydraulic fluid (hydraulic pump seal leak), dissolved metal traces (identification of wearing parts), or wear indicators (trace components).

The breather outlet 2 further comprises a microwave generator and a continuous wave laser (not specifically shown) disposed in the upper portion 4 of the breather outlet 2. The microwave generator and laser are connected to and powered using cables 8. Alternatively, the cables may comprise an optical fibre so as to allow the laser to be located outside of the fluid conduit but to transmit laser light into the fluid conduit.

The microwave generator comprises a waveguide splitter which effectively divides the output of the microwave generator into two discrete sources. The waveguide splitter also directs the two sources in different directions, with the second source being targeted further downstream than the first source. The microwave generator further comprises an attenuator which attenuates the microwaves of the first source.

The laser is focussed on a position between the targets of the first and second microwave sources.

The lower portion 6 comprises a plurality of optical sensors 10 which are disposed around the circumference of the lower portion 6. The sensors transmit signals through cables 12, such as optical fibre cables. Alternatively, the sensors 10 may be located remotely and the optical fibre cables may transmit light to the sensors 10. The sensors 10 may be optically or electronically multiplexed to reduce weight.

A wire mesh or gauze 14 is provided downstream of the microwave generator and the sensors 10. Whilst the wire mesh 14 allows fluid to flow therethrough, it prevents microwaves from passing further down the fluid conduit and out of the breather outlet 2. The wire mesh 14 therefore contains the microwaves within the breather outlet 2.

A safety interlock (not shown) may be provided to prevent the microwave generator and laser from being operated if the breather outlet is not assembled or is misassembled. For example, the safety interlock may be provided between the upper and lower portions 4, 6 of the fluid conduit to ensure that the upper and lower portions 4, 6 are correctly connected in order to prevent radiation from exiting the breather outlet 2. In combination with the wire mesh 14, the safety interlock ensures that the apparatus operates in a safe manner.

In use, the microwaves from the first microwave source are directed towards the dispersion flowing through the fluid conduit of the breather outlet 2. As the microwaves have been attenuated by the attenuator they have insufficient intensity to vaporise the oil droplets and other particulate matter in the dispersion. Instead the microwaves are reflected by the particles causing the microwaves to deviate from their original trajectories. The scattering of the microwaves by the particles can be used in a scattering measurement to determine characteristics of the particles. For example, the size and number of oil droplets can be calculated from the trajectories of the microwaves.

The dispersion is subsequently exposed to the laser as it passes through the fluid conduit. The laser is focussed on a single particle or on a small number of particles (relative to the total number present) which have been stimulated by the microwaves. Preferably this is near the centre of the conduit.

The laser first applies a relatively low power pre-heat pulse. The pre-heat pulse heats but does not vaporise the particles.

Subsequently, the laser applies a second relatively high power pulse (i.e. the second pulse is more powerful than the first pre-heat pulse). The second pulse heats the particles to a very high temperature where they emit visible and invisible light. This laser induced incandescence (LII) can be detected by the sensors 10. The heat added to the particle or droplet during the first laser pulse can be measured from the infrared radiation emitted therefrom. This may be measured just before the application of the second pulse to provide a measurement of droplet size and speed.

The emission signal resulting from the laser induced incandescence is characteristic of the particulate matter producing it. Furthermore, the emission signal is proportional to the volume fraction of the particles.

Each sensor 10 may be filtered so as to receive only certain frequencies/wavelengths of light. Accordingly, each sensor is configured to detect different particles which may be present in the dispersion, thus allowing the composition of the dispersion to be determined. This also provides a measure of the volume fraction or number of oil droplets in the dispersion.

As described previously, the droplet or particle size can also be estimated by measuring the increase in temperature as a result of the first laser pulse and with a knowledge of the energy imparted by the pulse.

As the droplets are flowing through the fluid conduit the centre of incandescence will shift over time. Consequently, the sensors may sample or image the emission signal over time to provide a measurement of the fluid flow rate. This may also allow the breather discharge pressure to be measured. Alternatively, the vaporisation of the droplets may be used to provide a measure of flow. Here, the vaporisation of the droplets leaves a hole in the dispersion where no droplets are present. The displacement of this hole over time may be monitored using the emission signal, thus allowing the flow rate to be calculated.

The spectrographic data is collected, reduced and trended to provide information to the engine health monitoring (EHM) system, where it can be used in combination with other EHM data to make predictions for remaining useful life of components, and to determine any action which needs to be taken.

For example, with lubricants in low consumption systems, the required action may be to add additional oil to the system, to add or replenish additives, or to perform a complete flush and refill.

The fluid management apparatus may also highlight changes in breather pressure and in the pressure drop across the breather which can be indicative of air system or oil system sealing problems. These changes may also be linked to variations in engine operation to provide a more accurate diagnosis.

The breather assembly and particularly the oil/air separator may be adaptable in response to the measurements made by the fluid monitoring apparatus. For example, the speed of rotation of the oil/air separator may be adjusted to alter the efficiency of the system. This may be used where oil consumption is required, where the oil is cold and thick, where the oil is aged, hot and thin, etc.

The present invention allows the consumption of oil to be monitored. Consequently, this also provides feedback on the condition and age of the remaining oil in the system. Therefore, the present invention enables high efficiency oil system breathers (oil/air separators) to be used without suffering from the disadvantages of degraded oil.

The present invention uses a continuous wave laser which has a much higher fluence (=flux/time) than a pulsed laser (around 120 $Jcm^{-2}$ versus approximately 0.2-5 $Jcm^{-2}$). With a pulsed laser, the particle must be heated very quickly, before heat is dissipated, principally by conduction to the surrounding gas. In contrast, the high fluence of a continuous wave laser allows heat to be supplied to the particle at the same time as it is being lost to the surrounding gas.

Furthermore, pulsed lasers with energies greater than around 10 mJ are limited to repetition rates of approximately 10 Hz (pulse speed). Consequently, a laser producing 10 ns long pulses will only illuminate a given volume for $10^{-7}$ s of the total exposure time. Particularly in flowing gas, this will limit sensitivity to levels where a significant number of particles are illuminated during each laser pulse. In ambient air, the particle count may be too low to be detected using a pulsed laser. However, a continuous wave laser allows single particles to be detected as they pass through the continuous wave laser beam.

The LII technique of the present invention has been demonstrated with an oil mass flow of approximately 0.7 mg per minute. This equates to the consumption of 1 liter of oil in over 18,000 hours of engine operation. The present invention is therefore suitable for even the most efficient breather systems available.

The microwaves from the second source are directed downstream and impinge on the remaining oil droplets and other particles contained in the dispersion downstream of the sensors 10. Here, the microwaves agitate and heat the oil causing it to vaporise and thus become invisible to the naked eye. Although it is preferred to heat the droplets until they completely evaporate, it is not necessary to fully evaporate the droplets and merely reducing them in size is sufficient; the overall object being to render the discharged fluid substantially invisible.

The present invention therefore reduces the quantity of unburnt hydrocarbons (oil) discharged to the atmosphere.

In practice, it may only be necessary or desirable to operate the fluid management apparatus at certain times rather than continuously. For example, since the discharged dispersion may be more visible at low speed, it may only be necessary to operate the apparatus while the aircraft is in contact with the ground. Accordingly, a weight-on-wheels signal (as known in the art) may be used to provide this indication. Furthermore, it may be desirable to operate the apparatus only when the oil is warm so that less pre-heat is required, at times when it is known that oil droplets are generated, and/or following the detection of an engine transient event, such as a fuel spike. Thus continuous monitoring is not necessary and for components with a long estimated life a once per flight sample may be sufficient.

The present invention is not limited to the management of a dispersion containing oil droplets and other contaminants present in a gas turbine engine. The invention may be applied to any application where it is desirable to monitor and/or treat a fluid containing particulate matter.

For example, the invention could be used to monitor the exhaust from a machining centre. Here, the exhaust flow may be monitored to determine an oil, cutting fluid, hydraulic oil, transmission oil, or coolant fluid composition and debris content. Air flow can also determine the condition of the filter and monitor the discharges to atmosphere.

The invention could also be used to monitor equipment and safety systems such as biological filters and fume cupboard filters in order to detect system problems and to provide predictions as to when maintenance, such as a filter change or a system scrub, will be required.

Moreover, the present invention is not limited to aircraft engines and may, for example, be applied to marine diesel engines, particularly for determining fuel composition.

Although the first and second microwave sources have been described as being provided by a common microwave generator, they may alternatively be provided by two distinct microwave generators.

Furthermore, the microwave generator may be replaced by a generator which produces other types of electromagnetic waves. For example, a generator producing ultrasonic waves, infrared radiation or gamma rays could be used. With this arrangement, the wire mesh 14 would be replaced by a suitable means of containing the electromagnetic radiation.

The invention claimed is:

1. A breather outlet comprising:

a fluid conduit for the passage of a dispersion containing particulate matter;

a laser arranged to provide laser light inside the fluid conduit; wherein, in use, the laser light heats the particulate matter sufficiently to generate incandescence;

one or more sensors for detecting the incandescence of the particulate matter so as to determine a characteristic of the dispersion;

an electromagnetic wave generator operable to provide electromagnetic waves inside the fluid conduit wherein the output of the electromagnetic wave generator is split and directed upstream of the laser light through an attenuator so as to so as to perform a scattering measurement and downstream of the laser light so as to vaporise at least a portion of the dispersion.

2. A breather outlet as claimed in claim 1, wherein the output is split by a waveguide splitter.

3. A breather outlet as claimed in claim 1, wherein the intensity of the electromagnetic waves is lower at the upstream position than at the downstream position.

4. A breather outlet as claimed in claim 1, wherein the electromagnetic wave generator is a microwave generator.

5. A breather outlet as claimed in claim 1, wherein the one or more sensors are coupled to the fluid conduit by optical fibres.

6. A breather outlet as claimed in claim 1, wherein the sensors are electronically or optically multiplexed.

7. A breather outlet as claimed in claim 1, wherein the laser is configured to provide a first relatively low power pre-heat pulse and a second relatively high power pulse to induce incandescence in the particulate matter.

8. A breather outlet as claimed in claim 1, wherein the laser is a continuous wave laser.

9. A breather outlet as claimed in claim 1, further comprising a second laser, wherein the lasers intersect one another inside the fluid conduit.

10. A breather outlet as claimed in claim 9, wherein the lasers are diametrically opposed.

11. A breather outlet as claimed in claim 1, wherein the characteristic of the dispersion include one or more of:

(i) composition;

(ii) size of the particulate matter;

(iii) volume fraction of particulate matter;

(iv) flow rate of the dispersion;

(v) flight time of the particulate matter;

(vi) increase in temperature of the particulate matter; and (vii) fluid conduit discharge pressure.

12. A breather outlet as claimed in claim 1, further comprising a safety interlock which prevents the laser and/or electromagnetic wave generator from operating if the breather outlet is not assembled or is misassembled.

13. A gas turbine engine comprising a breather outlet as claimed in claim 1.

14. A method of using a breather outlet comprising:

passing a dispersion containing particulate matter through a fluid conduit of the breather outlet;

passing electromagnetic waves through the dispersion to perform a scattering measurement using a first portion of electromagnetic waves;

heating the particulate matter sufficiently with laser light to generate incandescence, wherein the first portion of electromagnetic waves is directed upstream of laser light;

detecting the incandescence of the particulate matter to determine a characteristic of the dispersion; and vaporising at least a portion of the dispersion using a second portion of electromagnetic waves directed downstream of the laser light.

* * * * *